United States Patent
Li et al.

(10) Patent No.: US 9,004,848 B2
(45) Date of Patent: Apr. 14, 2015

(54) FEEDING DEVICE

(71) Applicants: Hong Fu Jin Precision Industry (ShenZhen) Co., Ltd., Shenzhen, Guangdong Province (CN); Hon Hai Precision Industry Co., Ltd., Tu-Cheng, New Taipei (TW)

(72) Inventors: Bing Li, Shenzhen (CN); Bo Yang, Shenzhen (CN); Yong Zhang, Shenzhen (CN)

(73) Assignees: Hong Fu Jin Precision Industry (ShenZhen) Co., Ltd., Shenzhen (CN); Hon Hai Precision Industry Co., Ltd., New Taipei (TW)

( * ) Notice: Subject to any disclaimer, the term of this patent is extended or adjusted under 35 U.S.C. 154(b) by 208 days.

(21) Appl. No.: 13/628,245

(22) Filed: Sep. 27, 2012

(65) Prior Publication Data
US 2014/0010626 A1    Jan. 9, 2014

(30) Foreign Application Priority Data
Jul. 6, 2012    (CN) .......................... 2012 1 0233049

(51) Int. Cl.
*B65G 13/00*    (2006.01)
*B65G 59/02*    (2006.01)
*G01N 35/02*    (2006.01)
*G01N 35/00*    (2006.01)
*B65G 57/30*    (2006.01)

(52) U.S. Cl.
CPC .......... *G01N 35/028* (2013.01); *G01N 35/0099* (2013.01); *B65G 57/302* (2013.01); *B65G 13/00* (2013.01); *B65G 59/02* (2013.01)

(58) Field of Classification Search
CPC ...... B23P 21/00; B23P 19/001; B23P 21/004; B65G 65/00; B65G 60/00; B65G 61/00; B65G 57/302; B65G 59/026; B65G 35/06; B65G 47/5181; B65G 59/02; B65G 57/165; B65B 69/00; B65B 5/068; G01N 2035/0425; G01N 2035/0427; Y10S 414/102; Y10S 206/821; Y10S 414/107; Y10S 414/108; Y10S 414/112; B23Q 7/10; B23Q 7/1431; B23Q 7/00
USPC ............... 414/222.1, 416.01, 416.03, 416.04, 414/416.05, 416.07, 795.3, 95.4, 795.6, 414/796.5, 796.7, 796.8, 796.9
See application file for complete search history.

(56) References Cited

U.S. PATENT DOCUMENTS 2,224,606 A * 12/1940 Neckel .......................... 271/212
4,541,762 A *  9/1985 Tischler et al. ............. 414/788.7

(Continued)

*Primary Examiner* — Gregory Adams
(74) *Attorney, Agent, or Firm* — Novak Druce Connolly Bove + Quigg LLP

(57) ABSTRACT

A feeding device includes a housing, a first conveying mechanism mounted on the housing, and a distribution mechanism. The housing forming a receptacle space includes a top surface defining a receiving opening communicated with the receptacle space. The distribution mechanism includes a slide platform slidably mounted on the top surface, a distribution member, and elastic members. The slide platform defines an unloading opening communicated with the receiving opening and a mounting groove adjacent to the unloading opening. The distribution member is movably mounted in the mounting groove. The elastic member elastically resists the distribution member to protrude out from the unloading opening. The stacked feeding trays resist the distribution member to move away from the unloading opening. When the top feeding tray is moved above the distribution member, the distribution member retracts by an elastic force to separate the top feeding tray from the stacked feeding trays located below.

17 Claims, 4 Drawing Sheets

(56) References Cited

U.S. PATENT DOCUMENTS

| | | | |
|---|---|---|---|
| 4,588,341 A * | 5/1986 | Motoda | 414/788.4 |
| 4,684,308 A * | 8/1987 | Dorner | 414/795.3 |
| 5,190,434 A * | 3/1993 | Miura et al. | 414/609 |
| 5,207,727 A * | 5/1993 | Pearce et al. | 414/792.7 |
| 5,672,040 A * | 9/1997 | Kimura et al. | 414/403 |
| 5,919,025 A * | 7/1999 | Kimura et al. | 414/403 |
| 6,648,587 B1 * | 11/2003 | McMunigal et al. | 414/800 |
| 7,360,984 B1 * | 4/2008 | Sugiyama et al. | 414/798.1 |

* cited by examiner

FEEDING DEVICE

BACKGROUND

1. Technical Field

The present disclosure relates to feeding devices, and particularly to a feeding device for transferring feeding trays.

2. Description of the Related Art

In an automatic production line, an automatic feeding device is used to improve work efficiency. The feeding trays must be manually distributed one by one. And then, each feeding tray will be transferred to a robot arm station by a conveying line. Thus, the work efficiency is affected negatively.

Therefore, there is room for improvement within the art.

BRIEF DESCRIPTION OF THE DRAWINGS

The components in the drawings are not necessarily drawn to scale, the emphasis instead being placed upon clearly illustrating the principles of the present disclosure. Moreover, in the drawings, like reference numerals designate corresponding parts throughout several views, and all the views are schematic.

DETAILED DESCRIPTION

Figure 1:
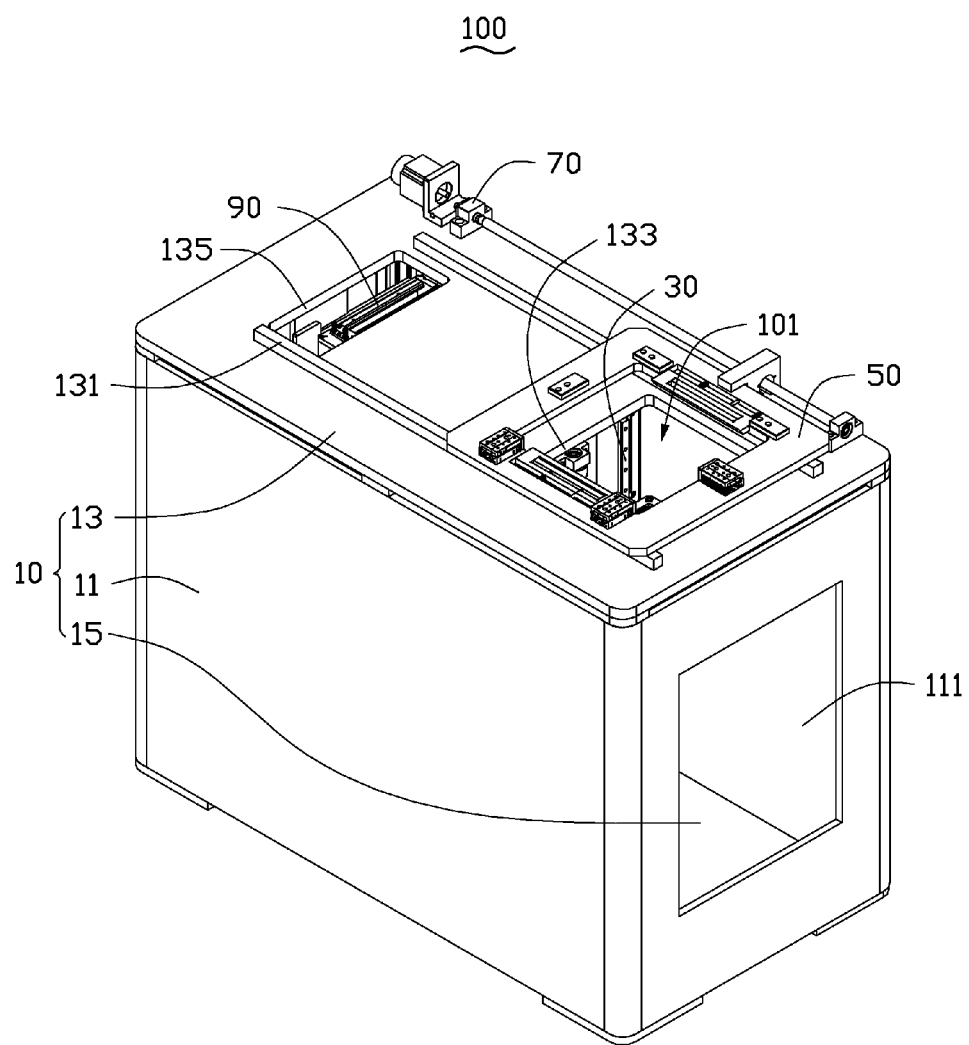
FIG. 1 is an assembled, isometric view of one embodiment of a feeding device with feeding trays, which includes a housing, a first conveying mechanism, a distribution mechanism, and a handling assistance mechanism.
Figure 2:
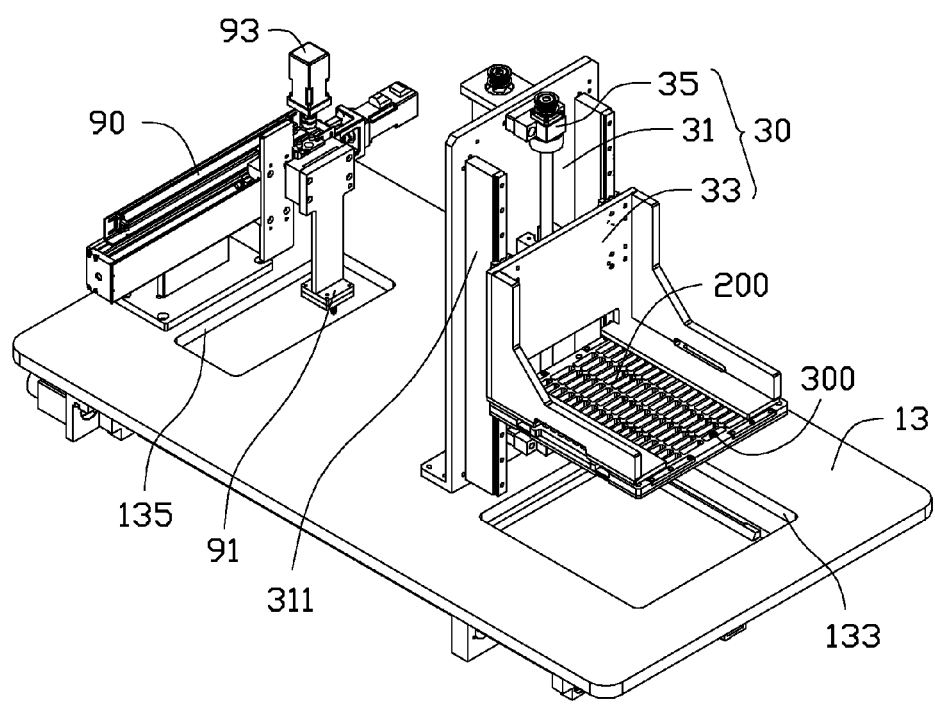
FIG. 2 is an assembled, isometric view of the first conveying mechanism and the handling assistance mechanism mounted on the housing in FIG. 1.

Referring to FIGS. 1 and 2, one embodiment of a feeding device 100 is used for transferring a plurality of feeding trays 200 one by one for the robot arm (not shown) to pick up. The feeding device 100 includes a housing 10, a first conveying mechanism 30, a distribution mechanism 50, a second conveying mechanism 70, and a handling assistance mechanism 90. The first conveying mechanism 30, the distribution mechanism 50, and the second conveying mechanism 70 are mounted on the housing 10. The first conveying mechanism 30 is received in the housing 10. In the illustrated embodiment, the feeding trays 200 are rectangular plate-shaped.

The housing 10 is a substantially hollow cube, and includes a top wall 13, a bottom wall 15 opposite to the top wall 13, and a peripheral wall 11 interconnecting the top wall 13 and the bottom wall 15. The top wall 13, the bottom wall 15, and the peripheral wall 11 cooperatively form a receptacle space 101. Two guide portions 131 are formed on a top surface of the top wall 13, extending along a lengthwise direction of the top wall 13 and parallel to each other. A receiving opening 133 and an operation opening 135 are defined on the top wall 13 between the guide portions 131, and in communication with the receptacle space 101. A feeding opening 111 is defined on the peripheral wall 11, communicating with the receptacle space 101 and adjacent to the receiving opening 133. In another embodiments, the number of the guide portions 131 can be changed as needed, such as one, three, or four.

The first conveying mechanism 30 is mounted in the housing 10, and is received in the receptacle space 101, for conveying the feeding trays 200 from the feeding opening 111 to the receiving opening 133. The first conveying mechanism 30 includes a base 31, a loading member 33, and a driving member 35. The base 31 is substantially L-shaped, and is mounted on an inner surface of the top wall 13 adjacent to the receiving opening 133. A pair of guide rails 311 is formed on the base 31 along a direction from the top wall 13 to the bottom wall 15. The loading member 33 is slidably mounted on the guide rails 311 to load the feeding trays 200. The driving member 35 is mounted on the base 31 to drive the loading member 33 sliding from the top wall 13 to the bottom wall 15 along the guide rails 311. In the illustrated embodiment, the driving member 35 is a leading screw. The driving member 35 can be a cylinder in another embodiment. In another embodiments, the number of the guide rails 311 can be changed as needed.

Figure 3:
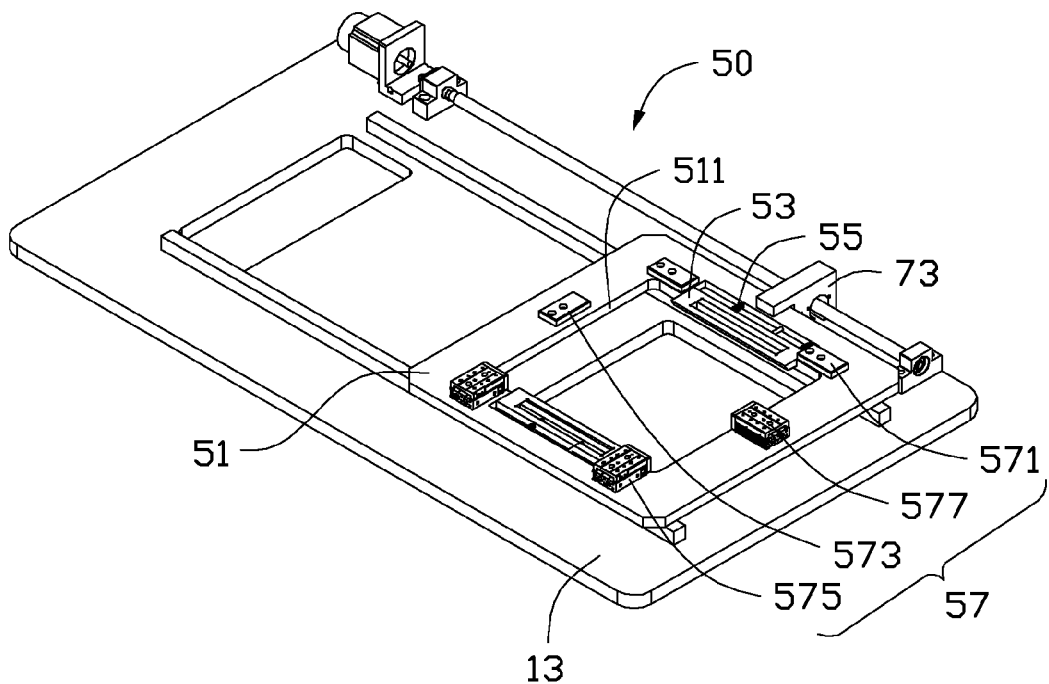
FIG. 3 is an assembled, isometric view of the distribution mechanism onto the top wall of the housing in FIG. 1.
Figure 4:
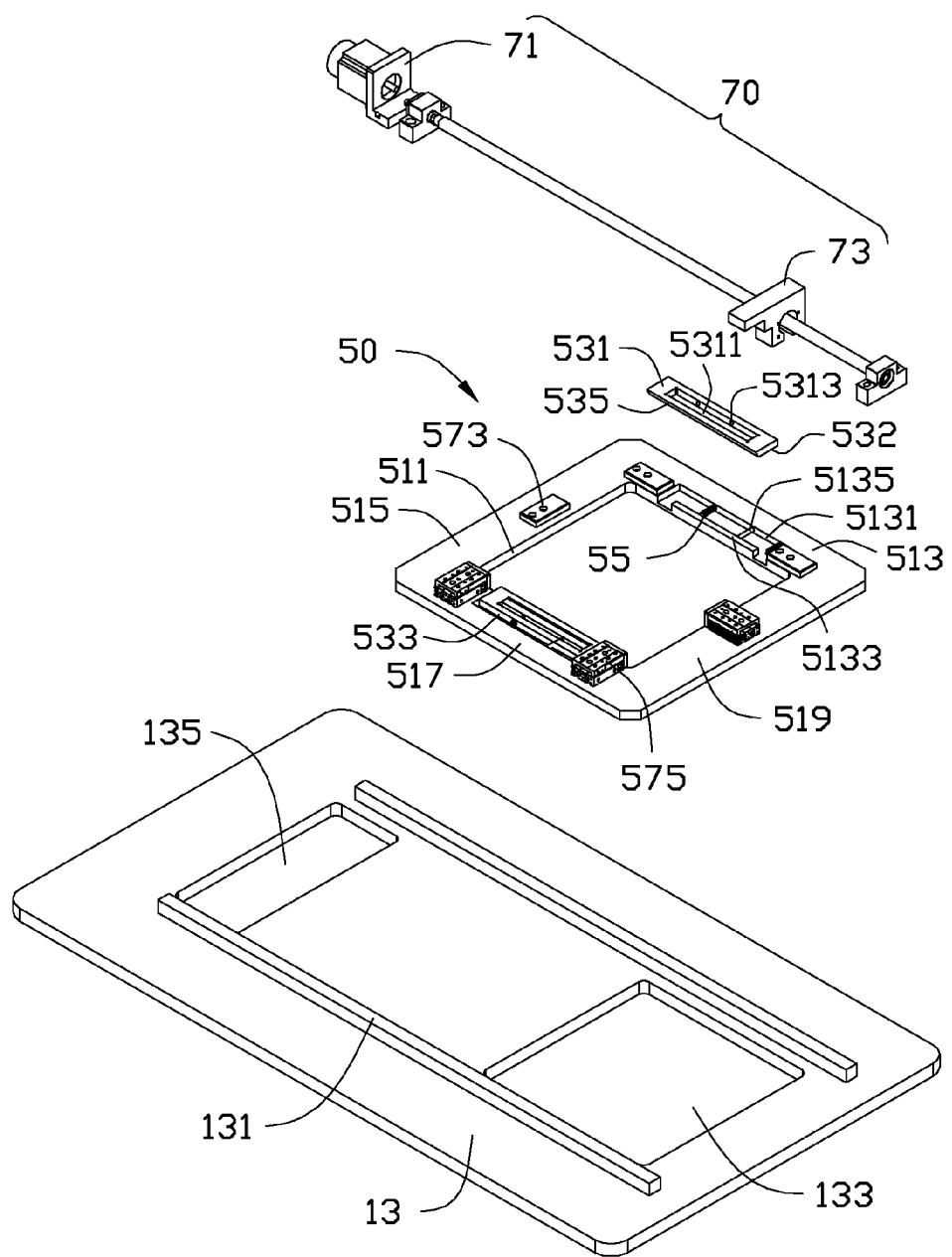
FIG. 4 is an exploded, isometric view of the distribution mechanism in FIG. 1

Referring to FIGS. 3 and 4, the distribution mechanism 50 is mounted on the top wall 13 of the housing 10, for distributing the stacked feeding trays 200 one by one. The distribution mechanism 50 includes a slide platform 51, a pair of distribution members 53, four elastic members 55, and a fixing assembly 57.

The slide platform 51 is plate-like, and is slidably mounted on the pair of guide portions 131. An unloading opening 511 is defined in a center of the slide platform 51. The unloading opening 511 is rectangular, and is communicated with the receiving opening 133. The feeding trays 200 are conveyed from the receiving opening 133 to the unloading opening 511. The slide platform 51 includes a first mounting surface 513, a second mounting surface 515, a third mounting surface 517, and a fourth mounting surface 519 interconnected one by one and located around the unloading opening 511. The first mounting surface 513 is parallel to the third mounting surface 517. The second mounting surface 515 is parallel to the fourth mounting surface 519. The first mounting surface 513 and the third mounting surface 517 are perpendicular to the second mounting surface 515 and the fourth mounting surface 519, respectively. Two mounting grooves 5131 are defined on the edges of the first mounting surface 513 and the third mounting surface 517, respectively, adjacent to and communicated with the unloading opening 511. Each of the first mounting surface 513 and the third mounting surface 517 further includes a stopper portion 5133 formed on a bottom surface of the mounting grooves 5131 adjacent to the unloading opening 511. Two slide shafts 5135 are mounted between each stopper portion 5133 and a sidewall of the mounting groove 5131 facing toward the stopper portion 5133. In other embodiments, the number of the slide shafts 5135 can be changed as needed, such as one, three, or four.

The distribution member 53 is substantially a rectangular block, and includes a top surface 531, a mounting sidewall 533 connected perpendicularly to the top surface 531, and an inclined sidewall 535. The mounting sidewall 533 is opposite to the inclined sidewall 535. A slot 5311 is defined on a center of the top surface 531. Each distribution member 53 is movably mounted in the corresponding mounting groove 5131. The stopper portion 5133 passes through the slot 5311. In an illustrated embodiment, a size of the slot 5311 is greater than the size of the stopper portion 5133. Two through holes 5313 are defined on the mounting sidewall 533. The slide shaft 5135 passes through the through hole 5313, such that the distribution member 53 can move along the slide shaft 5135. The inclined sidewall 535 is slanted toward the top surface 531. An angle between the inclined sidewall 535 and the top surface 531 is smaller than 90 degrees. In other embodiments, the number of the distribution members 53 can be changed as needed, such as one, three, or four.

Each elastic member 55 is sleeved on one slide shaft 5135. Opposite ends of the elastic member 55 resist elastically to a sidewall of the mounting groove 5131 and the mounting surface 533, respectively, such that the distribution member 53 is protruded out from the unloading opening 511, and the distribution member 53 can retract to its original state or position under an elastic force. The slide shafts 5135 can be omitted. In that case, opposite ends of the elastic member 55 are connected to a side surface of the mounting groove 5131 and the mounting surface 533, respectively. In other embodiments, the number of the elastic members 55 can be changed as needed, such as one, three, or four.

When the loading member 33 loaded with the feeding trays 200 moves toward the slide platform 51, and the feeding tray 200 located at the top thereof resists against the inclined sidewall 535, the distribution members 53 move away from the unloading opening 511, and the elastic members 55 can be compressed. When the feeding tray 200 located at the top thereof moves above the distribution member 53, the distribution members 53 retract under the elastic force. Thus, the feeding trays 200 are distributed one by one.

The fixing assembly 57 is mounted on the slide platform 51, for fixing the feeding tray 200 in a distributed manner. The fixing assembly 57 includes two first positioning members 571, a second positioning member 573, two first holding members 575, and a second holding member 577. The first positioning members 571 are securely placed on the first mounting surface 513, adjacent to two sides of the mounting groove 5131. The second positioning member 573 is securely placed on the second mounting surface 515. The first holding members 575 are securely placed on the third mounting surface 517 opposite to the first positioning members 571, respectively. The second holding member 577 is securely placed on the fourth mounting surface 519 opposite to the second positioning member 573. The first positioning members 571, the second positioning member 573, the first holding members 575, and the second holding member 577 cooperatively fix the feeding tray 200. In the illustrated embodiment, the first holding members 575 and the second holding member 577 are cylinders. The first holding members 575 and the second holding member 577 can be leading screws in another embodiment. In other embodiments, the number of the first positioning member 571, the second positioning member 573, the first holding member 575, and the second holding member 577 can be changed as needed.

The second conveying mechanism 70 includes a driving member 71 and a connection member 73, for conveying the slide platform 51 to the operation opening 135. The driving member 71 is mounted on the top wall 13 of the housing 10 adjacent to the first mounting surface 513 of the slide platform 51. In the illustrated embodiment, the driving member 71 is a leading screw. The driving member 71 can be a cylinder. The connection member 73 is connected to the slide platform 51 at the first mounting surface 513, and interconnects the driving member 71 and the slide platform 51, so that the slide platform 51 can be moved by the driving member 71 to the operation opening 135. In other embodiments, the second conveying mechanism 70 can be omitted, and the slide platform 51 with the feeding trays 200 arranged in distributed configuration can be moved by hand.

The handling assistance mechanism 90 includes a pushing member 91 and a driving member 93 placed on the top wall 13. The pushing member 91 is connected to the driving member 93, and can be moved by the driving member 93 to protrude out of the operation opening 135, for pushing the workpiece 300 out of the feeding tray 200. Thus, it is convenient for the robot arm to handle the workpieces 300. In other embodiments, the handling assistance mechanism 90 can be omitted, and the workpieces 300 are handled by the robot arm directly.

In assembly, the first conveying mechanism 30 is first mounted in the housing 10, and the loading member 33 is positioned below the receiving opening 133; secondly, the slide platform 51 is slidably mounted on the guide portions 131, the distribution members 53 are sleeved on the stopper portions 5133, respectively, and then the slide shafts 5135 with the elastic members 55 pass through the through holes 5313, respectively; thirdly, the fixing assembly 57 is mounted on the slide platform 51; fourthly, the driving member 71 is mounted on the top wall 13, and the connection member 73 is connected to the first mounting surface 513; finally, the handling assistance mechanism 90 is mounted in the housing 10.

In use, the feeding trays 200 are first stacked and placed on the loading member 33 through the feeding opening 111, and then the driving member 35 is started or turned on to drive the loading member 33 to move toward the receiving opening 133, so that the stacked feeding trays 200 resist the inclined sidewall 535, and the elastic members 55 are compressed. Secondly, when the feeding tray 200 located at the top stacking layer thereof is moved above the distribution member 53, the distribution member 53 retracts away from abutting feeding tray 200 by the elastic force, and then the distribution member 53 is placed to be rested between two feeding trays 200 which are stacked together. Thirdly, the fixing assembly 57 is actuated or started to fix the feeding tray 200 located at the top stacking layer to be held together for separating from the remaining feeding trays 200 located in the remaining stacking layers or levels below, and the second conveying mechanism 70 is turned on to convey the feeding tray 200 at the top stacking layer to be separated from the remaining feeding trays 200 to the operation opening 135. Finally, the handling assistance mechanism 90 pushes the workpieces 300 out of the feeding tray 200 (from the top stacking layer/level that has been separated), and the workpieces 300 are handled by the robot arm. Repeat the above mentioned steps to distribute or transport the feeding trays 200 from the feeding opening 111 to the operation opening 135 continually.

It is to be understood, however, that even through numerous characteristics and advantages of the disclosure have been set forth in the foregoing description, together with details of the structure and function of the embodiments, the disclosure is illustrative only, and changes may be made in detail, especially in matters of shape, size, and arrangement of parts within the principles of the embodiments to the full extent indicated by the broad general meaning of the terms in which the appended claims are expressed.

What is claimed is:

1. A feeding device for transferring a plurality of stacked feeding trays containing a plurality of workpieces, comprising:
   a housing forming a receptacle space, and comprising a top wall defining a receiving opening communicated with the receptacle space;
   a first conveying mechanism mounted in the housing for conveying the stacked feeding trays to move toward the receiving opening; and
   a distribution mechanism comprising:
      a slide platform slidably mounted on the top wall, defining an unloading opening communicated with the receiving opening and at least one mounting groove adjacent to the unloading opening;
      a distribution member movably mounted in the at least one mounting groove and comprising a top surface and an inclined sidewall slanted to the top surface, an angle between the inclined sidewall and the top surface being smaller than 90 degrees; and an elastic member placed between the distribution member and a sidewall of the mounting groove, for elastically resisting the distribution member to protrude out from the unloading opening, wherein the stacked feeding trays are conveyed by the first conveying mechanism toward the receiving opening until the feeding tray located at a top stacking layer resists the inclined sidewall of the distribution member to move away from the unloading opening, and when the feeding tray located at the top stacking layer of the stacked feeding trays is moved above the top surface of the distribution member, the distribution member is returned to its original state by an elastic force produced by the elastic member being compressed to separate the feeding tray at the top stacking layer from the remaining stacked feeding trays;

wherein at least one slide shaft is formed on the sidewall of the mounting groove, the distribution member further comprises a mounting sidewall defining at least one through hole and opposite to the inclined sidewall, the slide shaft passes through the through hole, and the elastic member is sleeved on the slide shaft, such that the distribution member is capable of moving along the slide shaft.

2. The feeding device of claim 1, wherein a stopper portion is formed on a bottom surface of the mounting groove adjacent to the unloading opening, the slide shaft is mounted between the stopper portion and the sidewall of the mounting groove, the top surface of the distribution member defining a slot is connected perpendicularly to the mounting sidewall, and the stopper portion passes through the slot.

3. The feeding device of claim 1, wherein the feeding device further comprises a second conveying mechanism comprising a driving member and a connection member for conveying the slide platform, the driving member is mounted on the top wall of the housing adjacent to the slide platform, and the connection member interconnects the driving member and the slide platform, so that the slide platform and the feeding tray is capable of moving by the driving member.

4. The feeding device of claim 1, wherein at least one guide portion is formed on the top wall adjacent to the unloading opening, and the slide platform is movably mounted on the guide portion, so that the slide platform is capable of moving along the guide portion.

5. The feeding device of claim 1, wherein the first conveying mechanism further comprises a base, a loading member, and a driving member connected to the loading member, the base is mounted on an inner surface of the top wall adjacent to the receiving opening, the loading member is slidably mounted on the base to load the stacked feeding trays, and the driving member is mounted on the base to drive the loading member toward the receiving opening.

6. The feeding device of claim 5, wherein at least one guide rail is formed on the base, and the loading member is slidably mounted on the guide rail.

7. The feeding device of claim 1, wherein an operation opening is defined on the top wall communicated with the receptacle space.

8. The feeding device of claim 7, wherein the feeding device further comprises a handling assistance mechanism comprising a pushing member, the pushing member is movable to protrude out of the operation opening, for pushing the workpiece out of the feeding tray.

9. The feeding device of claim 1, wherein the distribution mechanism further comprises a fixing assembly comprising at least one positioning member and at least one holding member, the positioning member and the holding member are mounted on the slide platform oppositely and on two sides of the unloading opening, so that the feeding tray is fixed by the positioning member and the holding member cooperatively.

10. A feeding device for transferring a plurality stacked feeding trays containing a plurality of workpieces, comprising:

a housing forming a receptacle space, and comprising a top wall defining a receiving opening communicated with the receptacle space;

a first conveying mechanism mounted in the housing for conveying the stacked feeding trays to move toward the receiving opening; and a distribution mechanism comprising:

a slide platform slidably mounted on the top wall, defining an unloading opening communicated with the receiving opening and at least one mounting groove adjacent to the unloading opening;

a distribution member movably mounted in the at least one mounting groove, wherein the distribution member comprises a top surface and an inclined sidewall slanted to the top surface, and an angle between the inclined sidewall and the top surface is smaller than 90 degrees;

an elastic member placed between the distribution member and a sidewall of the mounting groove, for elastically resisting the distribution member to protrude out from the unloading opening; and a second conveying mechanism comprising a driving member mounted on the top wall adjacent to the slide platform and a connection member interconnecting the driving member and the slide platform for conveying the slide platform;

wherein at least one slide shaft is formed on the sidewall of the mounting groove, the distribution member further comprises a mounting sidewall defining at least one through hole and opposite to the inclined sidewall, the slide shaft passes through the through hole, and the elastic member is sleeved on the slide shaft, such that the distribution member is capable of moving along the slide shaft.

11. The feeding device of claim 10, wherein a stopper portion is formed on a bottom surface of the mounting groove adjacent to the unloading opening, the slide shaft is mounted between the stopper portion and the sidewall of the mounting groove, the top surface of the distribution member defining a slot is connected perpendicularly to the mounting sidewall, and the stopper portion passes through the slot.

12. The feeding device of claim 10, wherein at least one guide portion is formed on the top wall adjacent to the unloading opening, and the slide platform is movably mounted on the guide portion, so that the slide platform is capable of moving along the guide portion.

13. The feeding device of claim 10, wherein the first conveying mechanism further comprises a base, a loading member, and a driving member connected to the loading member, the base is mounted on an inner surface of the top wall adjacent to the receiving opening, the loading member is slidably mounted on the base to load the stacked feeding trays, and the driving member is mounted on the base to drive the loading member toward the receiving opening.

14. The feeding device of claim 13, wherein at least one guide rail is formed on the base, and the loading member is slidably mounted on the guide rail.

15. The feeding device of claim 10, wherein an operation opening is defined on the top wall communicated with the receptacle space, the feeding device further comprises a handling assistance mechanism comprising a pushing member, the pushing member is movable to protrude out of the operation opening, for pushing the workpiece out of the feeding tray.

16. The feeding device of claim 10, wherein the distribution mechanism further comprises a fixing assembly comprising at least one positioning member and at least one holding member, the positioning member and the holding member are mounted on the slide platform oppositely and on two sides of the unloading opening, so that the feeding tray is fixed by the positioning member and the holding member cooperatively.

17. A feeding device for transferring a plurality of stacked feeding trays containing a plurality of workpieces, comprising:
   a housing forming a receptacle space, and comprising a top wall defining a receiving opening communicated with the receptacle space;
   a first conveying mechanism mounted in the housing for conveying the stacked feeding trays toward the receiving opening; and
   a distribution mechanism comprising:
      a slide platform slidably mounted on the top wall, defining an unloading opening communicated with the receiving opening and at least one mounting groove adjacent to the unloading opening;
      a distribution member movably mounted in the at least one mounting groove; and
      an elastic member placed between the distribution member and a sidewall of the mounting groove, for elastically resisting the distribution member to protrude out from the unloading opening;
      wherein at least one slide shaft is formed on the sidewall of the mounting groove, the distribution member further comprises a mounting sidewall defining at least one through hole and opposite to the inclined sidewall, the slide shaft passes through the through hole, and the elastic member is sleeved on the slide shaft, such that the distribution member is capable of moving along the slide shaft.

* * * * *